017# United States Patent [19]
Link

[11] 3,980,884
[45] Sept. 14, 1976

[54] PROCESS AND APPARATUS FOR DETERMINING THE CONCENTRATION OF A SUSPENSION
[75] Inventor: Hans Link, Reutlingen, Germany
[73] Assignee: Institut Dr. Friedrich Forster, Prufgeratebau, Reutlingen, Germany
[22] Filed: Mar. 24, 1975
[21] Appl. No.: 561,193

[30] Foreign Application Priority Data
Mar. 25, 1974 Germany............................ 2414314

[52] U.S. Cl................................. 250/302; 324/38
[51] Int. Cl.²................... G01R 33/12; G01T 1/161
[58] Field of Search ........... 250/302, 356, 365, 373; 324/38

[56] References Cited
UNITED STATES PATENTS
2,267,999  12/1941  Switzer .............................. 250/302
3,402,349  9/1968  Parker .............................. 250/302
3,573,979  4/1971  Honjo .............................. 250/302

*Primary Examiner*—Harold A. Dixon
*Attorney, Agent, or Firm*—George J. Netter

[57] ABSTRACT

A representative reading for the concentration of a suspension of luminous and magnetizable particles is provided in every case, even when luminous but non-magnetizable particles are also present. That is, the presence of non-magnetizable luminous particles in the suspension have no effect on the determination. A rotating wheel-like member has its lowermost portions immersed in a supply of the magnetic particle suspension in a fluid carrier. The circumferential periphery includes a permanent magnet having a gap extending continuously around the periphery and covered over by a plastic rim. As the wheel-like member rotates, the magnetic particle suspension forms a bead along the magnet gap. Ultra violet radiation directed onto the bead causes the magnetic particles to fluoresce and the degree of fluorescence is measured by photosensitive means.

13 Claims, 3 Drawing Figures

U.S. Patent  Sept. 14, 1976  3,980,884
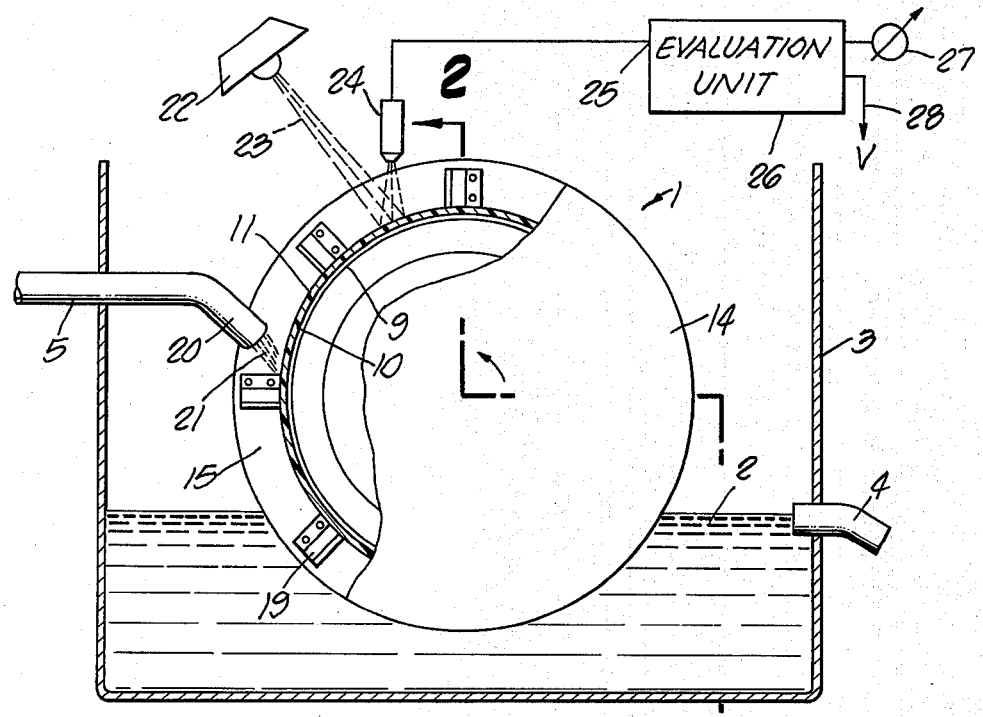
FIG. 1.
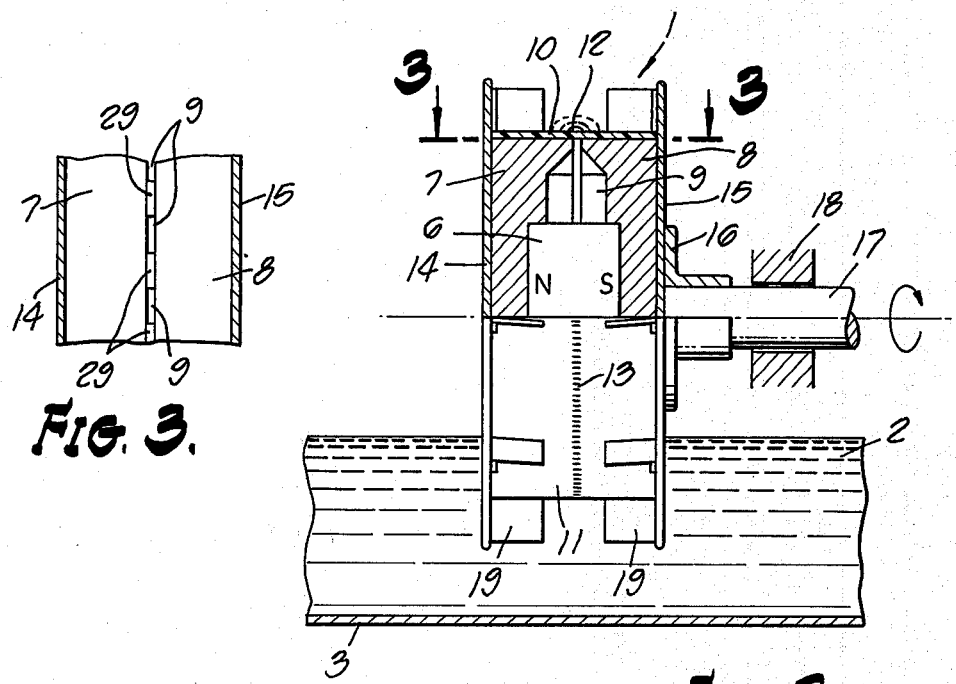
FIG. 3.
FIG. 2.

PROCESS AND APPARATUS FOR DETERMINING THE CONCENTRATION OF A SUSPENSION

The present invention relates generally to a process and apparatus for determining the concentration of a magnetic particle suspension consisting of magnetic powder particles to which fluorescent or luminous pigments have been added and a carrier fluid in which the particles are suspended.

BACKGROUND OF THE INVENTION

It is becoming increasingly important to determine and hold constant the concentration of magnetic particle suspensions, since to an increasing extent quantitative inspection procedures are making use of the magnetic particle method, whereas in the past these procedures have been mostly accomplished purely qualitatively. Since it has become the practice to optically scan accumulations of fluorescent magnetic powder particles and to use the luminous intensity of the particles accumulating at the location of a defect to indicate its depth, changes in the concentration of the suspension directly affect the result obtained, namely, reading of the depth of the defect.

Published West German patent application DT — AS 2 100 013 makes known a process for holding constant the concentration of a fluid bath used in testing metal objects for cracks, breaks or fissures. In this process, the concentration of the bath, which is required as a control variable, is determined by photosensitive detection means. Although this process has a certain degree of success in preventing powder particle impoverishment in the bath, to date it has not been possible to achieve fully satisfactory results, for the reasons which will be now given. When used for inspection purposes magnetic powder suspensions deteriorate to some extent, not only because their concentration is constantly weakened as particles are extracted to accumulate at the leakage flux locations of the items under inspection, but also because increasingly as a function of time, the shells split away from the paticles, which shells bind the fluorescent or luminous pigments to the particles. This means that the luminous intensity of a suspension includes that of luminous particles which are not, or no longer, bound to magnetic powder particles, and non-magnetizable particles are useless for inspection by magnetic techniques. The process referred to above, in which the concentration of a suspension is measured on the basis of the luminous intensity of random particles, gives unambiguous readings only when the particles whose luminous intensity is being measured actually have a magnetizable core. This, however, cannot be fully assured even when the suspension is freshly produced.

OBJECT AND SUMMARY OF THE INVENTION

A primary object of the present invention, therefore, is the provision of a process and apparatus which gives a representative reading for the concentration of luminous and magnetizable particles in the suspension in every case, even when luminous but non-magnetizable particles are also present. That is, the non-magnetizable luminous particles have virtually no effect. A rotating wheel-like member has its lowermost portions immersed in a supply of magnetic particle suspension in a fluid carrier. The circumferential periphery includes a permanent magnet having a gap extending continuously around the periphery and covered over by a plastic rim. As the wheel-like member rotates, the magnetic particle suspension forms a bead along the magnet gap. Ultra violet radiation directed onto the bead causes the magnetic particles to fluoresce and the degree of fluorescence is measured by photosensitive means.

DESCRIPTION OF THE DRAWINGS

FIG. 1 is a schematic diagram of apparatus for carryinng out the process according to the invention;

FIG. 2 is a partially sectional view taken along the line 2—2 of FIG. 1; and

FIG. 3 is a sectional view taken along line 3—3 of FIG. 2 showing an alternate embodiment.

DESCRIPTION OF PREFERRED EMBODIMENTS

Reference is now made to the drawing and particularly FIG. 1. As shown there, a rotor 1 is partially submerged in a suspension 2 of fluorescent magnetic powder particles in a fluid carrier, held in a container 3. This suspension 2 in the container 3 is maintained in close contact with the suspension used in say, a defect detecting process, the concentration of which it is desired to determine. This can be achieved, for example, by having the suspension, which escapes through the overflow 4, pass to the defect detection area, be applied by spray nozzles to the magnetized items being examined, and then as it flows off the items, after which it is collected in a tray and returned through the inlet pipe 5 back to the container 3. It is also possible for other inspection procedures to insert the container 3 into the circuit of the suspension used in the inspection, or the container 3 can be in a by-pass line from the circulating suspension, provided it is insured that the concentration of the suspension in the by-pass is the same as that in the main flow. In the simplest case, the inspection can take place in the container 3 itself, the items under inspection being immersed in the suspension 2 and then scanned for concentrations of fluorescent particles.

The construction of the rotor 1 can best be explained by further reference to FIG. 2, in which the rotor is shown in section in the upper part and in its actual view in the lower part. The core of the rotor 1 comprises a disc-shaped permanent magnet 6 which is polarized axially. Two shells 7 and 8 made of magnetically weak material enclose the permanent magnet 6 concentrically and with it form a closed magnetic circuit except for an annular gap 9. An endless plastic band 10 is shrunk onto the circumference of the two shells 7 and 8, giving a smooth, outwardly directed surface 11, from which leakage flux 12 extends all around the circumference. Under the influence of the leakage flux 12 when the rotor 1 is set in motion, a bead 13 of magnetic powder particles accumulates on the surface 11. The two shells 7 and 8 are closed off at their outer edges by the plates 14 and 15. The rotor 1 is also linked by a flange 16 to a shaft 17, which is journaled in a bearing 18 and driven by a power source (not shown). A number of oblique paddles 19 are fitted around the circumference on the inner sides of the plates 14 and 15.

The inlet pipe 5 is arranged so that when the apparatus is operating, a jet 21 protruding from the pipe orifice 20 strikes the surface 11. A source 22 of ultra-violet light is fitted above the rotor 1, and its beam 23 illuminates an area of the surface 11. A photosensitive element 24 is fitted opposite the illuminated area of the surface 11 and electrically linked to the input 25 of an evaluation unit 26. The measuring instrument 27 connected to the evaluation unit 26 provides a display which is proportional to the level of luminous intensity picked up by the element 24. A voltage signal proportional to this same level is also delivered at the output 28.

The apparatus described is used as follows. Firstly, the rotor 1 is set in motion. This can be achieved by means of an external drive, via shaft 17, or alternatively, the jet 21 may be arranged in such a manner that it will be directed against the paddles and drive the rotor 1. The paddles 19 have the function of agitating the suspension 2 and insuring an even distribution of the magnetic powder particles within the tank 3. Under the influence of the leakage flux 12 protruding through the surface 11, the magnetic powder particles accumulate in the manner described and form a bead 13. formation of this bead 13 is further helped by the phenomenon that where the rotor emerges from the suspension 2 small quantities of the suspension are drawn up by the paddles and then slowly run back down, along the gap 9. As the rotor 1 turns, the bead 13 is continuously carried through the area which is illuminated by the lightsource 22 and scanned by the element 24, and in which the pigments of the magnetic powder particles are excited by the ultra violet light to give off a bright radiation. Given a constant strength of the ultra violet light from the source 22, the luminous intensity picked up by the element 24 is dependent solely on the number of luminous particles which have accumulated in the bead 13, and, therefore, because of the constant value of the leakage flux 12, on the concentration of magnetizable and luminous particles in the suspension 2. The display on the instrument 27, and the voltage at the output 28, can therefore be taken as directly indicating the concentration under investigation.

The jet pouring from the orifice 20 of the inlet pipe 5 onto the surface 11 directly strikes the bead 13 of magnetic powder particles. The smoothness of the surface 11 makes it easy for the jet to wash off the bead, so that when the surface 11 passes through the suspension 2 once more, a new bead 13 can be formed. This process means that the display always reflects the actual concentration existing at the time it is examined. Alternatively, the bead 13 can be cleaned off by means of a brush fitted below the surface of the suspension 2 and in contact with the surface 11, which will sweep the magnetic powder particles from the smooth surface and enable a new bead 13 to form.

The voltage signal at the output 28 of the evaluation unit 26, which is proportional to the concentration of the suspension, can be utilized in a variety of ways. One version, as described in the referenced published German patent specification, is to make use of it to control the entry of new magnetic powder particles into the suspension, thus keeping the concentration constant. It is contemplated to use the measured variable at output 28 to regulate the sensitivity of the optical system, for example, a television camera, scanning the luminous intensity of the defect locations. In many cases, it will be advantageous to use a combination of both versions.

In the apparatus described so far, for simplicity of description a permanent magnet has been used to create a magnetic flux projecting from a surface. Other means, however, can also be used to create the leakage flux, such as a ferro-magnetic body through which passes an electric current of a constant magnitude, and on whose surface a groove of a defined depth runs obliquely to the magnetic field formed. It is, however, important in this case that the characteristics of the surface should be such as to allow the accumulated magnetic powder particles to be removed easily, such as, for example, by applying a film of paint to the surface.

The apparatus as shown in FIGS. 1 and 2 has a substantially constant, ring-shaped pattern of leakage flux 12 which extends around the circumference of the rotor 1. Over one revolution of the rotor 1, therefore, the luminous intensity level to be picked up by the photosensitive element 24 varies only slightly. This means, that given a relatively low speed of rotation of the rotor 1, the amplifier of the evaluation unit 26 would have to transmit frequencies practically down to a zero level. Disturbance variables, such as, for example, a slow drift of the operating point of the element 24 might thus be transmitted, also. This disadvantage can be easily avoided by modulating the luminous intensity level with an alternating quantity, for example, by chopping the beam from the light-source 22, or alternatively, the input voltage to the evaluation unit 26.

A more advantageous possibility, however, is to use leakage flux at the gap 9 which is intermittent along the scanning path rather than the constant flux 12. To accomplish production of intermittent magnetic flux along the rotor periphery, a preferred manner is that shown in FIG. 3. As shown there, instead of a continuous gap 9, a plurality of spaced magnetic shorting bars 29 extend across the gap. Accordingly, the magnetic flux will only extend outwardly of the rotor between the bars 29. In use, the magnetic particle suspension will form a series of spaced groups or clumps of adhered suspension and these will produce a corresponding alternating signal when scanned by the photosensitive element.

What I claim is:

1. A process for determining the concentration of a suspension of magnetic powder particles in a fluid carrier to which fluorescent or luminous pigments have been added, the improvement comprising:
    directing a continuous magnetic field of predetermined uniform character outwardly from a surface;
    flowing the suspension along and in contact with the surface from which the magnetic field extends to produce a relative movement between the surface and the suspension; and
    measuring the luminous intensity of the particles accumulating on the surface under the influence of the magnetic field where it extends from the surface.

2. A process as in claim 1, in which the relative movement between the surface and the suspension is created by periodically immersing portions of the surface in the suspension, and measuring the luminous intensity of the particles accumulating at the points where the magnetic flux extends from these portions of the surface.

3. A process as in claim 2, in which the periodic immersion of portions of the surface in the suspension is achieved by rotation of the surface, which is partially immersed in the suspension.

4. A process as in claim 1, including the further step of removing the magnetic particles from the surface after measurement of the luminous intensity thereof.

5. A process as in claim 4, in which the removal of the particles is achieved by directing a jet of the suspension thereagainst.

6. A process for determining the concentration of a fluorescent magnetic powder suspended in a liquid carrier, comprising the steps of:
   locating the magnetic powder and liquid carrier in a container;
   moving a surface having magnetic flux extending outwardly thereof into and out of contact with said magnetic powder and carrier in said container whereby said powder adheres to said surface in the areas where the magnetic flux extends outwardly;
   irradiating the powder adhering to the surface with a light beam to produce fluorescence thereof;
   detecting the amount of fluorescence produced by photosensitive means; and
   generating an electric signal of value functionally related to the amount of fluorescence and thereby the concentration of said magnetic powder suspension in said carrier.

7. Apparatus for determining the concentration of a fluorescent magnetic powder suspended in a liquid carrier located in a container, comprising:
   a generally cylindrical rotor rotatably mounted about its cylindrical axis with a circumferential portion thereof maintained in contact with said suspension;
   means mounted on said rotor for producing defined magnetic flux externally of said rotor and extending along the rotor circumference whereby a certain amount of said magnetic powder suspension adheres to the rotor circumference in the region of said defined external magnetic flux;
   a light beam directed onto said rotor circumferential periphery for fluorescing the adhered magnetic powder suspension; and
   photosensitive means for producing an electric signal responsive to fluorescence of the adhered magnetic powder suspension.

8. Apparatus as in claim 7, in which the magnetic flux extends from the surface of the rotor along a continuous line around the circumference of the rotor.

9. Apparatus as in claim 7, in which the magnetic flux extends intermittently outwardly from the surface of the rotor along a defined line.

10. Apparatus as in claim 7, in which the circumferential surface of the rotor is formed from a smooth skin.

11. Apparatus as in claim 7, in which the suspension is located in a container with an inlet pipe and a discharge pipe; and
   a jet of suspension from the inlet pipe is directed onto the circumferential surface of the rotor in such a way that the adhered magnetic powder particles are removed therefrom.

12. Apparatus as in claim 7, in which the rotor circumference includes at least one paddle which mixes the suspension in the container as it moves therethrough.

13. Apparatus as in claim 7, in which paddles are fitted around the circumference of the rotor; and
   a jet of suspension from the inlet pipe is directed onto the paddles to rotatably drive the rotor.

* * * * *